United States Patent [19]

Foster

[11] Patent Number: 4,500,382
[45] Date of Patent: Feb. 19, 1985

[54] METHOD OF MANUFACTURE OF RESIN FILM PRECISION BIOMEDICAL ARTICLE

[75] Inventor: William J. Foster, Chicago, Ill.

[73] Assignee: Transilwrap Company, Inc., Chicago, Ill.

[21] Appl. No.: 503,347

[22] Filed: Jun. 10, 1983

[51] Int. Cl.³ .............................................. B29C 19/02
[52] U.S. Cl. ........................................ 156/272.8; 3/13; 156/251
[58] Field of Search .......................... 156/272.8; 3/13; 156/251, 515, 380.9

[56] References Cited

U.S. PATENT DOCUMENTS

| 3,981,230 | 9/1976 | Lee | 156/380.1 |
| 4,069,080 | 1/1978 | Osborne | 156/272.8 |
| 4,251,887 | 2/1981 | Anis | 3/13 |
| 4,414,051 | 11/1983 | Bose | 156/272.8 |

Primary Examiner—David Simmons
Attorney, Agent, or Firm—Kinzer, Plyer, Dorn & McEachran

[57] ABSTRACT

A method of manufacture of an article such as a corneal implant glide, formed of two resin film elements, each of which must be precision cut to a predetermined size and configuration with smooth, burr-free edges and with a narrow welded band of precisely controlled characteristics joining the two film elements along mating edges, comprises the steps of aligning two resin films in overlapping relation and constraining the films to maintain them in surface-to-surface contact with an exposed area at least as large as that required for the finished article. A laser beam of extremely small dot-like cross-section, preferably about 0.005 inch (0.127 millimeter) diameter, is directed to impinge upon the exposed area of the films and the beam is then moved, relative to the exposed film area, along a precisely controlled path corresponding to the outline of the article, including the aforementioned mating edges, to cut the two films to the precise required shape and simultaneously weld the two films together.

9 Claims, 8 Drawing Figures

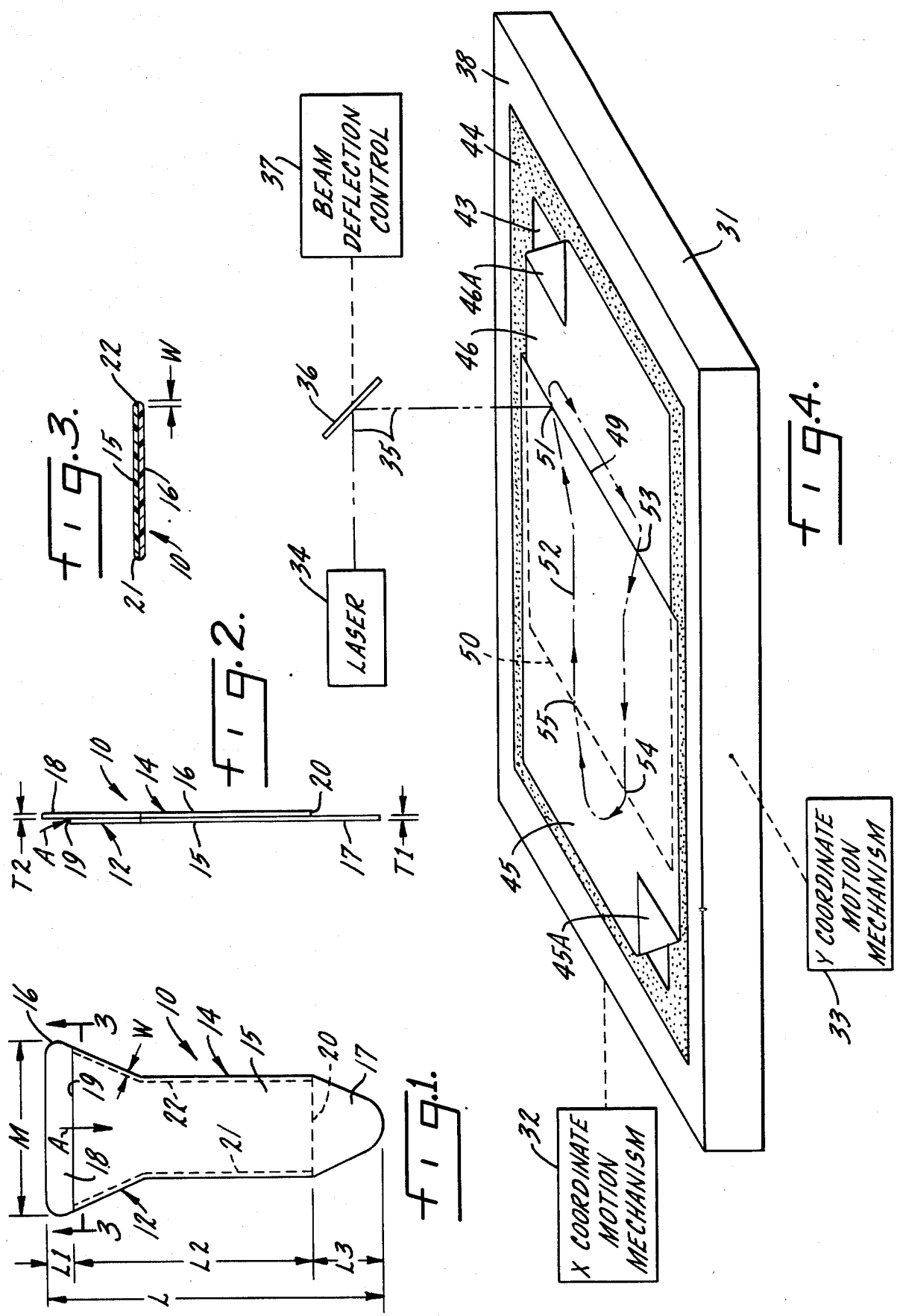

METHOD OF MANUFACTURE OF RESIN FILM PRECISION BIOMEDICAL ARTICLE

BACKGROUND OF THE INVENTION

Articles formed of resin film are coming into use in various biomedical fields, particularly eye surgery. One such article is a corneal implant glide used in the placement of corneal implants in the eyes of patients requiring such implants, due to removal of cataracts, etc. Implant glides of varying sizes and shapes are required for different patients. Some are used for anterior implants, behind the outer lens of the eye. Others are employed in posterior implants, positioned behind both lenses.

In a corneal implant glide of this kind, two resin film elements are joined together with a pocket or passageway between the two films. Of course, the resins used for the films must have characteristics acceptable for biomedical uses. In articles of this kind, particularly the aforementioned corneal implant glides, it is often necessary that the resin film be extremely thin; film thicknesses of 0.0009 inch (0.023 millimeter) and less are commonly employed.

The manufacturing requirements for articles of this kind are extremely demanding. The size and configuration of the article must be controlled within very close tolerances, usually plus or minus 0.0003 inch (0.0076 mm) or less. Any edges must be smooth and free of burrs and projections. Particles clinging to the edges or to any other point on the article are not permissable. For those articles formed of two thicknesses of resin film, the welded joint between the two films should be made as narrow as possible to keep the size of the article within tolerance limits.

Conventional manufacturing techniques for processing resin films have yielded poor results when applied to the fabrication of this type of precision article for biomedical use. Thus, with conventional thermal weld and die cut equipment, in which cutting of the film members from larger stock and edge welding of those members are performed as separate steps, it is extremely difficult and frequently virtually impossible to maintain accurate registration between the die cutting and welding operations, regardless of the sequence in which the two basic steps are performed. Furthermore, the weld lines are generally too wide, uneven, and unduly subject to variations in configuration. Using conventional "thermal kiss and cut" techniques, the edge welds are uneven and the outline cut of the article is often ragged in character. Radio frequency sealing and cutting methods can be held to close enough tolerances to produce reasonably satisfactory articles, but are limited to the use of plasticized vinyl resins which are not generally suitable for biomedical applications.

SUMMARY OF THE INVENTION

It is a principal object of the present invention, therefore, to provide a new and improved method of manufacture of a precision article for biomedical use, such as a corneal implant glide, of the kind comprising overlapping thin-film resin members of precisely predetermined size and configuration welded together along one or more mating edges with narrow, controlled welds not appreciably wider than the thicknesses of the resin films.

A particular object of the present invention is to provide a new and improved method of manufacture of a corneal implant glide or like tiny article suitable for biomedical use, fabricated from thin resin films having thicknesses of the order of 0.0005 to 0.015 (0.013 to 0.038 mm) in which the welds are extremely narrow and the edges of the articles are free of burrs, particles, and other irregularities, with the overall size and shape of each article held to extremely close tolerances.

A specific object of the invention is to provide a new and improved process for manufacturing corneal implant glides and other similar minute resin-film articles for biomedical applications that can be held to close tolerances, that is applicable to a wide variety of film resins, yet is relatively simple and economical.

Accordingly, the invention relates to a method of manufacture of a precision article for biomedical use, such as a corneal implant glide, of the kind comprising first and second overlapping resin film members, each having a preselected thickness and a precise predetermined size and configuration, with the overlapping portions of the two resin film members corresponding in size and configuration and joined together along one or more mating edges; the method comprises the steps:

A. aligning a first resin film, having a thickness corresponding to that required for the first film member but larger in area than the first film member, in at least partially overlapping relation to a second resin film, having a thickness corresponding to that required for the second film member but larger in area than the second film member, the overlapping portions of the two films being larger in area than the overlapping portions of the resin film members of the article;

B. constraining the two resin films to maintain areas of the two aligned films larger than the finished article in essentially flat, surface-to-surface contact, exposed from one side;

C. directing a laser beam having a maximum cross-sectional dimension no larger than the combined thicknesses of the two resin films, to impinge upon the exposed area of the aligned, constrained films; and D. moving the laser beam relative to the exposed areas of the aligned, constrained films, along a predetermined path corresponding precisely to the size and configuration of the peripheral outline of the finished article to cut the two resin film members from the resin films and simultaneously to weld the resin film members together, in a narrow, controlled band not appreciably wider than the combined thicknesses of the two resin films, along their mating edges.

BRIEF DESCRIPTION OF THE DRAWINGS

FIG. 1 is a plan view, on a greatly enlarged scale, of a corneal implant glide constituting an example of the kind of precision article for biomedical use manufactured by the method of the present invention;

FIG. 2 is a side view of the article of FIG. 1 with the thickness of the resin films forming the article greatly exaggerated;

FIG. 3 is a sectional view taken approximately as indicated by line 3—3 in FIG. 1, with the thickness of the resin films again greatly exaggerated;

FIG. 4 is a perspective view of one type of apparatus that may be utilized in carrying out the method of the invention;

DESCRIPTION OF THE PREFERRED EMBODIMENTS

Figure 5:
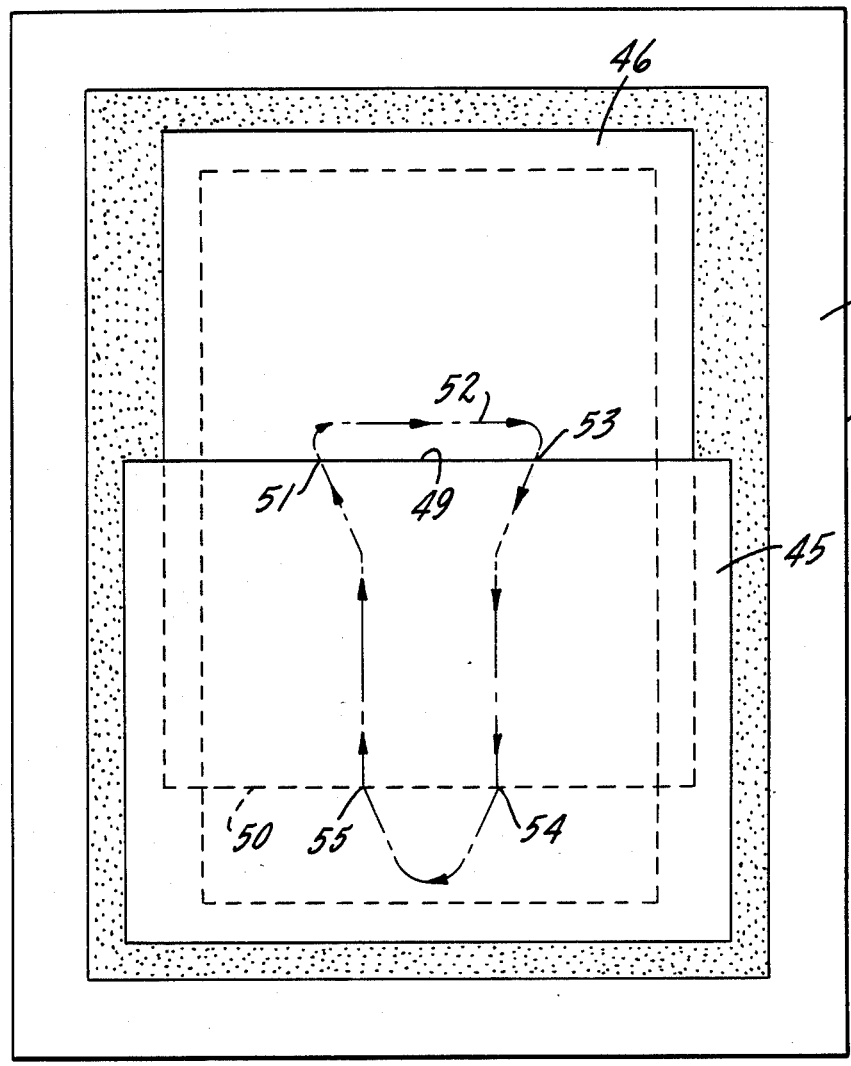
FIG. 5 is a plan view of a part of the apparatus of FIG. 4.

FIGS. 1–3 afford an illustration, on a greatly enlarged scale, of a corneal implant glide 10 constituting one example of a precision article for biomedical use of the kind manufactured by the method of the present invention. Glide 10 comprises first and second overlapping resin film members 15 and 16. In the central portion of glide 10 the two resin film members 15 and 16 overlap in a sleeve portion 14. The first film member 15 includes an extension or flap portion 17, extending below the lower edge 20 of the second film member 16. In the head portion 12 of the glide 10, the second film member 16 includes an extension or stage portion 18 extending beyond the edge 19 of the first film member 15.

The overlapping portions of the two resin film members 15 and 16 in glide 10 correspond precisely in size and configuration to each other and are joined together along their mating edges by welds 21 and 22 to form the sleeve 14. The nature of the welds 21 and 22 is quite critical. The width W of each weld should be extremely narrow, typically less than the total thickness $T1+T2$ of the two resin film members 15 and 16. In a typical glide 10, T1 and T2 may each be in the range of 0.0005 inch to 0.002 inch (0.0127 mm to 0.051 mm). Nevertheless, welds 21 and 22 must be strong because, during use of glide 10 a corneal implant is moved through the space between the two film members 15 and 16 as generally indicated by the arrow A in FIGS. 1 and 2. Glide 10 is very small in size, having an overall length L, in a typical embodiment, of 23.75 mm and a maximum width M of 11.5 mm; in that glide, the stage length L1 is 2 mm, sleeve length L2 is 16.75 mm, and flap length L3 is 5 mm. On the other hand, the size and configuration of glide 10 must be controlled with great precision, typically to tolerances of the order of plus and minus 0.008 millimeter.

Figure 6:
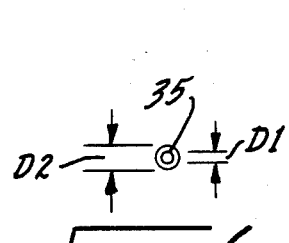
FIG. 6 illustrates the dimensional and operational characteristics of a laser beam used in performance of the method of the invention.

FIGS. 4 and 5 illustrate one form of apparatus that may be utilized in carrying out one embodiment of the method of manufacture of the present invention. This apparatus comprises a precision X-Y table 31, the movements of table 31 being controlled by an X coordinate motion mechanism 32 and a Y coordinate motion mechanism 33. Table 31, preferably an aluminum table, is positioned beneath a laser device 34 which generates a beam 35 of very small cross-sectional configuration. Laser 35, for example, may be a carbon dioxide laser having a power output of fifty to three hundred fifty watts; other types of laser can also be used. As shown in FIG. 6, the beam 35 has a maximum cross-sectional dimension or diameter D1 of approximately 0.005 inch (0.127 mm). The effective "spread" of such a beam is limited, as indicated by dimension D2, to about 0.006 inch (0.152 mm). As shown in FIG. 4, the laser beam 35 is directed toward the X-Y table 31 by a deflector 36. The alignment of beam 35 relative to table 31 may be adjusted by varying the alignment of deflector 36 as indicated by a beam deflection control 37.

A film mounting member 44 is positioned on the upper surface 38 of table 31. Member 44 is itself formed of a thin resin film surfaced on both sides with a light pressure sensitive adhesive and is of rectangular configuration with a central opening 43 that is substantially larger than the corneal implant glide 10 (FIG. 1). Member 44 may be formed in one piece as shown or can be formed by strips of plastic tape having both surfaces coated with a pressure sensitive adhesive.

A thin resin film 46 is aligned on the surface of table 31 with three edges of the film overlapping the pressure sensitive mounting member 44 so that film 46 is held flat on the surface of table 31. One edge 50 of film 46, which is to form the edge 20 of film member 16 in glide 10 (FIG. 1), is the only edge of film 46 that is not directly adhered to the table surface, using the apparatus shown in FIGS. 4 and 5. In a typical embodiment, film 46 is of polypropylene having a thickness of 0.0009 inch (0.023 mm).

A film 45 is aligned with film 46 on the surface 38 of the X-Y table 31, FIGS. 4 and 5. Typically, film 45 is a polypropylene film also having a thickness of 0.023 mm; however, films 45 and 46 need not be of the same thickness. Film 45 is wider than film 46 so that its side edges engage and adhere to the pressure sensitive surface of mounting member 44. Further, film 45 is long enough so that the end of the film also engages the pressure sensitive mounting member. Thus, the only edge of film 45 that is not held against the surface 38 of table 31 directly by engagement with mounting member 44 is the edge 49 which is to form the edge 19 of the completed corneal implant glide 10 (FIG. 1).

In FIG. 4, one corner 45A of the first film 45 is shown turned back from mounting member 44. Similarly, a corner 46A of the second resin film 46 is shown pulled away from the pressure sensitive mounting member 44. This has been done solely to afford a better illustration of the shape of the underlying mounting member 44; in actual practice, film corners 45A and 46A would be in flat adherring relation to mounting member 44.

With the two films 45 and 46 aligned with each other as shown in FIGS. 4 and 5, in partially overlapping relation, and constrained flat against each other adjacent the table surface 38, laser 34 is energized and is directed to impinge at a starting point 51 on a closed path 52 that corresponds precisely to the size and configuration of the peripheral outline of the corneal implant glide 10 to be manufactured. Initial positioning of the impingement point 51 for beam 35 may be adjusted by means of beam deflection control 37 and deflector 36. The coordinate motion mechanisms 32 and 33 are then actuated to move table 31 so that beam 35 traverses path 52, tracking the path with closely controlled accuracy. This relative movement of the laser beam along path 52 is carried out at a relatively low speed, typically of the order of eighty inches per minute (33.9 mm/sec.) for a fifty watt laser. Relatively slow speeds of this nature are necessary to enable the laser beam to cut through films 45 and 46 and, in the overlapping portion of the films between edges 49 and 50, to weld the two films together.

Thus, as laser beam 35 traverses path 52, it first cuts out the stage portion 18 of glide 10 (FIG. 1), which consists solely of a portion of the second film 46. When the path crosses edge 49 of film 45 at point 53, and continues along path 52 to point 54, the laser beam cuts through both of the films 45 and 46 and forms the edge weld band 22 for the central sleeve 14 of glide 10 (FIG.

1). Between points 54 and 55 in FIGS. 4 and 5, the laser beam cuts the flap portion 17 of the glide. From point 55 the laser beam continues along path 52 back to point 51, cutting through both layers of film and forming the narrow edge weld band 21 of sleeve 14 (FIG. 1). Thus, the movement of laser beam 35 along path 52 completes the manufacture of the corneal implant guide 10.

With a laser beam as described (D1 about 0.127 mm) the overall effective width of the films affected by the beam in transversing sections 53–54 and 55–51 of path 52 is about 0.004 inch (0.102 mm). However, a central portion of the path, about 0.002 inch (0.051 mm) wide, is vaporized and removed by suction. This leaves an effective seal width W (FIGS. 1 and 3) of approximately 0.001 inch (0.025 mm) along the edge welds 21 and 22 of glide 10.

Figure 7:
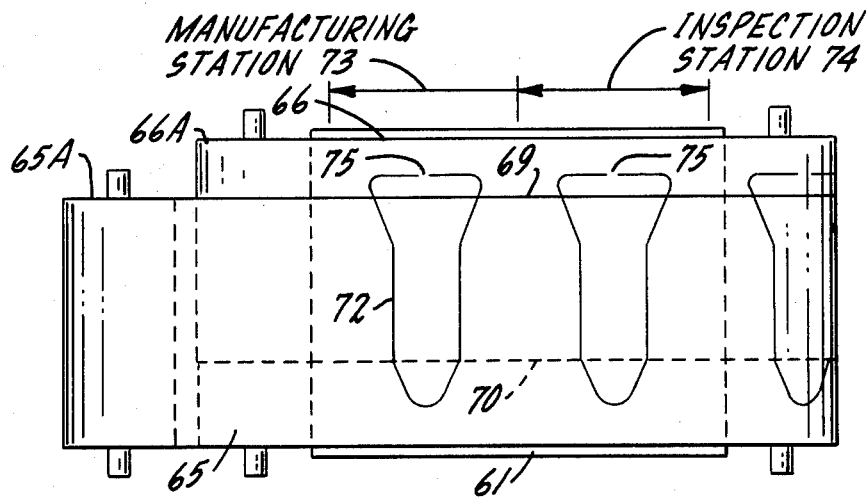
FIG. 7 is a plan view of another form of apparatus that may be utilized in carrying out the method of the invention.
Figure 8:
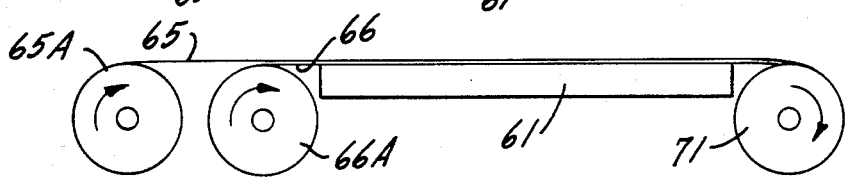
FIG. 8 is a side elevation view of the apparatus of FIG. 7.

FIGS. 7 and 8 illustrate another and substantially different type of apparatus that may be utilized to carry out the method of the invention in the manufacture of corneal implant glides 10 and other similar minute, precision controlled resin film biomedical articles. The apparatus of FIGS. 7 and 8 comprises a flat stationary support or table 61. A first resin film 65 is fed from a supply roll 65A across the surface of table 61 toward a takeup roll 71. A second resin film 66 is fed from a supply roll 66A across the surface of table 61 toward the takeup roll 71, beneath film 65. The two films 65 and 66 are maintained in precise alignment with each other so that they are in accurate partially overlapping alignment between the edge 69 of film 65 and the edge 70 of film 66. The supply and takeup rolls 65A, 66A and 71 are located slightly below the upper surface of table 61 and a light tension is maintained on both films, across table 61, so that the two films are held flat against each other on the support surface afforded by the table.

In this embodiment of the invention, a small-diameter laser beam (not shown) is directed to impinge upon the two overlapping and constrained films 65 and 66, and follows a closed path 72 conforming to the size and configuration of the peripheral outline of the desired corneal implant glide at a first location on table 61, identified as a manufacturing station 73. In this apparatus it is still possible to provide the requisite relative movement between the films 65, 66 and the laser beam by moving table 6, provided rolls 65A, 66A and 71 are mounted on and move with table 61. On the other hand, the necessary movement for the laser beam may be provided by an appropriate deflector and deflection control. In the course of movement of the beam along the cutting and welding path 72, the beam may be interrupted briefly to provide one or more gaps 75 in the cut/weld line. These gaps should be quite small, preferably no more than 0.1 inch (0.25 mm) and should be formed in a part of the article (e.g. the stage portion, as shown) that does not contact the patient.

When one glide has been cut from films 65 and 66 at manufacturing station 73, with the two film members forming the glide welded to each other as previously described, the folms are advanced to bring the completed glide to an adjacent portion of table 61 identified as inspection station 74. The glide remains entrained in the two films due to the minute gaps 75 in the cut/weld line of formation for the glide. Subsequently, the glides are rolled up, with the remainder of the film, on takeup roll 71. In this manner, a continuing strip containing a multiplicity of glides can be formed by the manufacturing process of the present invention, available for subsequent removal from the strip when use is required.

A variety of other techniques can be utilized in aligning two resin films and constraining the films in essentially flat surface-to-surface contact, exposed from one side, as is necessary to the practice of the method of the invention. Thus, a vacuum table can be employed as a support for the films during the cutting and welding operation performed by the laser beam. As long as one of the films is somewhat larger than the other, effective alignment and surface contact can be maintained. Another way to accomplish the requisite alignment and constraint of the films for practice of the invention is to utilize a hold-down arrangement like an embroidery hoop, tensioning the films lightly and maintaining them in good surface contact for the cutting and welding operations performed simultaneously by the laser beam.

Although polypropylene film is a preferred material for glide 10, the method of the invention is not limited to this specific resin; it is applicable to most thermoplastic resins, including styrenes, acetates, polyethylenes, polyolefins, butyrates and thermoplastic polyesters.

I claim:

1. The method of manufacture of a precision article for biomedical use, such as a corneal implant glide, of the kind comprising first and second overlapping resin film members, each having a preselected thickness and a precise predetermined size and configuration, with the overlapping portions of the two resin film members corresponding in size and configuration and joined together along one or more mating edges, comprising the following steps:
    A. aligning a first resin film, having a thickness corresponding to that required for the first film member but larger in area than the first film member, in at least partially overlapping relation to a second resin film, having a thickness corresponding to that required for the second film member but larger in area than the second film member, the overlapping portions of the two films being larger in area than the overlapping portions of the resin film members of the article;
    B. constraining the two resin films to maintain areas of the two aligned films larger than the finished article in essentially flat, surface-to-surface contact, exposed from one side;
    C. directing a laser beam having a maximum cross-sectional dimension no larger than the combined thicknesses of the two resin films, to impinge upon the exposed area of the aligned, constrained films; and
    D. moving the laser beam relative to the exposed areas of the aligned, constrained films, along a predetermined path corresponding precisely to the size and configuration of the peripheral outline of the finished article to cut the two resin film members from the resin films and simultaneously to weld the resin film members together, in a narrow, controlled band not appreciably wider than the combined thicknesses of the two resin films, along their mating edges.

2. The method of manufacturing a precision article according to claim 1 in which the maximum cross-sectional dimension of the laser beam is of the order of 0.127 millimeter and the width of the welded band between the two resin film members is of the order of 0.025 millimeter.

3. The method of manufacturing a precision article according to claim 2 in which the combined thicknesses of the two films is of the order of 0.102 millimeter.

4. The method of manufacturing a precision article according to claim 1, in which the first film member of the finished article includes an extension portion that extends beyond one edge of the second film member for a preselected extension distance, and in which:
- in step A the films are aligned with the first film extending beyond one edge of the second film by a distance appreciably larger than the preselected extension distance; and
- in step D the laser beam cuts the extension portion of the first film member to precise size and configuration without welding to the second film member.

5. The method of manufacturing a precision article according to claim 4 in which the maximum cross-sectional dimension of the laser beam is of the order of 0.01 millimeter and the width of the welded band between the two resin film members if of the order of 0.2 millimeter or less.

6. The method of manufacturing a precision article according to claim 1 in which the two resin films are positioned on a flat support and the edges of the two resin films are held on the support by a pressure sensitive adhesive.

7. The method of manufacturing a precision article according to claim 1 in which the resin films are elongated webs each extending from a feed location adjacent to and slightly below one edge of a flat support to a take-up location adjacent to and slightly below the opposite edge of the support, and in which each film is held under light tension between its feed location and the take-up location, during steps B through D, to maintain the films in flat, surface-to-surface contact.

8. The method of manufacturing a precision article according to claim 1 in which the two resin films are maintained on a flat support by vacuum.

9. The method of manufacturing a precision article according to claim 1 in which both films are polypropylene, each film having a thickness in a range of 0.013 to 0.38 millimeter.

* * * * *